US00PP25879P3

(12) United States Plant Patent
Danziger

(10) Patent No.: US PP25,879 P3
(45) Date of Patent: Sep. 8, 2015

(54) ***CHRYSANTHEMUM* PLANT NAMED 'DCHRYATRED'**

(50) Latin Name: ***Chrysanthemum* hybrid**
Varietal Denomination: DCHRYATRED

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 40 days.

(21) Appl. No.: 13/999,324

(22) Filed: Feb. 10, 2014

(65) Prior Publication Data

US 2015/0230382 P1 Aug. 13, 2015

(51) Int. Cl.
*A01H 5/02* (2006.01)

(52) U.S. Cl.
USPC ..... Plt./298

(58) Field of Classification Search
USPC ..... Plt./298
CPC ..... A01H 5/0255; A01H 5/025; A01H 5/02
See application file for complete search history.

*Primary Examiner* — Kent L Bell
(74) *Attorney, Agent, or Firm* — Cassandra Bright

(57) ABSTRACT

A new and distinct *Chrysanthemum* cultivar named 'DCHRYATRED' is disclosed, characterized by large flowers, unique color, good heat and cold tolerance, vigorous growth, and good vase life. The new variety is a *Chrysanthemum*, normally used for commercial cut flower production.

1 Drawing Sheet

Latin name of the genus and species: *Chrysanthemum* hybrid.

Variety denomination: 'DCHRYATRED'.

BACKGROUND OF THE INVENTION

The new *Chrysanthemum* cultivar is a product of a planned breeding program conducted by the inventor, Gavriel Danziger, in Moshav Mishmar Hashiva, Israel. The objective of the breeding program was to produce new *Chrysanthemum* varieties for cut flower commercial applications. The open pollination resulting in this new variety was made during November of 2008.

The seed parent is the unpatented, proprietary seedling variety referred to as *Chrysanthemum* 'CH-8-501'. The pollen parent is unknown as the new variety was produced from an open pollination breeding program. The new variety was discovered in November of 2009 by the inventor in a group of seedlings resulting from the 2008 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during February of 2010 and has shown that the unique features of this cultivar are stable and reproduced true to type in more than 10 successive generations.

SUMMARY OF THE INVENTION

The cultivar 'DCHRYATRED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCHRYATRED' These characteristics in combination distinguish 'DCHRYATRED' as a new and distinct *Chrysanthemum* cultivar:

1. Large flower size.
2. Unique red color.
3. Good heat and cold tolerance.
4. Good vase life.
5. Vigorous growth habit.

Plants of the new cultivar 'DCHRYATRED' are similar to plants of the seed parent, *Chrysanthemum* 'CH-8-501' in most horticultural characteristics, however, plants of the new cultivar 'DCHRYATRED' differs in the following ways:

1. Different flower color.
2. Larger flower size.
3. Longer pedicels.
4. Longer vase life.

COMMERCIAL COMPARISON

Plants of the new cultivar 'DCHRYATRED' are comparable to the commercial variety *Chrysanthemum* 'DANCHYAT' U.S. Plant Pat. No. 15,045. The two *Chrysanthemum* varieties are similar in most horticultural characteristics; however, the new variety 'DCHRYATRED' differs in the following ways:

1. Red flowers. The comparator flowers are white.
2. Fewer flowers per stem.
3. Longer photoperiodic reaction time to induce flowering.

Plants of the new cultivar 'DCHRYATRED' are also comparable to the unpatented commercial variety *Chrysanthemum* 'MARABOU'. The two *Chrysanthemum* varieties are similar in most horticultural characteristics; however, the new variety 'DCHRYATRED' differs in the following ways:

1. More flowers.
2. More vigorous.
3. Larger flowers.
4. Longer pedicels.

BRIEF DESCRIPTION OF THE PHOTOGRAPH

The accompanying photograph in FIG. 1 illustrates in full color a typical flower stem of 'DCHRYATRED' grown in a greenhouse. Age of the plant photographed is approximately 11 weeks from a planted a cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCHRYATRED' plants grown in a greenhouse in Moshav Mishmar Hashiva, Israel. The growing temperature ranged from 16° C. to 25° C. during the day and from 16° C. to 18° C. during the night. Chemical treatment used was Alar (B-Nine) used at a concentration of 3 gr/L. Measurements and numerical values represent averages of typical plant types.

Botanical classification: *Chrysanthemum* hybrid 'DCHRYATRED'.

PROPAGATION

Typical propagation material: Vegetative cuttings.
Time to rooting: 9 to 14 days at approximately 21-23° C.
Root description: Fibrous.

PLANT

Age of plant described: Approximately 11 weeks.
Height: Approximately 90-110 cm.
Plant spread: Approximately 16-20 cm.
Growth rate: Moderate.
Approximate quantity of lateral branches: Approximately 7-8 primary lateral branches and numerous secondary and tertiary lateral branches.
Length of lateral branches: Approximately 19-24 cm.
Diameter of lateral branches: Approximately 0.4 cm.
Texture of lateral branches: Pubescent.
Aspect/angle of branches: Upright.
Lateral branch strength: Strong.
Lateral branch color: Near RHS GREEN 137-B.
Internode length: Approximately 4-6 cm.
Number of leaves per lateral branch: Approximately one leaf in the base of the lateral branch.

FOLIAGE

Leaf:
- *Arrangement*.—Alternate.
- *Average length*.—Approximately 9-12 cm.
- *Average width*.—Approximately 5-5.5 cm.
- *Shape of blade*.—Pinnatipartite.
- *Apex*.—Rounded.
- *Base*.—Wedge shaped.
- *Attachment*.—Petiolate.
- *Margin*.—Serrate.
- *Texture of top surface*.—Slightly Warty.
- *Texture of bottom surface*.—Slightly Warty.
- *Appearance top surface*.—Matte.
- *Appearance bottom surface*.—Matte.
- *Leaf internode length*.—Approximately 4-5 cm.
- *Color*.—Young foliage upper side: Near RHS YELLOW-GREEN 147-A. Young foliage under side: Near RHS YELLOW-GREEN 147-B. Mature foliage upper side: Near RHS YELLOW-GREEN 147-A. Mature foliage under side: Near RHS YELLOW-GREEN 147-B.
- *Venation*.—Type: Pinnate. Venation color upper side: Near RHS YELLOW-GREEN 147-B. Venation color under side: Near RHS YELLOW-GREEN 147-B.

Petiole:
- *Petiole*.—Linear.
- *Length*.—2.5 cm.
- *Diameter*.—0.4 cm.
- *Pubescence*.—None.
- *Color*.—Near RHS YELLOW-GREEN 146-B.

FLOWER

Bloom period: Flowers after approximately 55 short days.
Vase life: 14-16 Days.
Other cultural improvements or features: None.

Bud:
- *Bud shape*.—Oblate.
- *Bud length*.—Approximately 1.5-2 cm.
- *Bud diameter*.—Approximately 1.5-2 cm.
- *Bud color*.—Near RHS YELLOW-GREEN 147-B.

Inflorescence:
- *Form*.—Corymb.

Flower:
- *Diameter of entire flower*.—Approximately 9.5 cm.
- *Depth of flower*.—Approximately 2-2.5 cm.
- *Width of disc*.—Approximately 2 cm.
- *Depth of disc*.—Approximately 1 cm.

Ray florets:
- *Number of ray florets*.—Avg. 30-32.
- *Length*.—Approximately 3.5-4.2 cm.
- *Width*.—Approximately 1-1.2 cm.
- *Apex shape*.—Obtuse.
- *Margin*.—Entire.

Color:
- *Ray florets*.—Upper surface at first opening: Near RHS RED 46-A. Upper surface at maturity: Near RHS RED 46-B. Upper surface at fading: Near RHS RED 42-A. Under surface at first opening: Near RHS ORANGE-RED-N34-A. Under surface at maturity: Near RHS ORANGE-RED-34-B. Under surface at fading: Near RHS ORANGE-RED-34-B.
- *Disc florets*.—Number of Disc Florets: 200-220. Length: Approximately 0.4-0.5 cm. Width: Approximately 0.1 cm. Shape: Bell shaped (campanulate). Margin: Entire. At first opening: Near RHS YELLOW-GREEN N144-A. At maturity: Near RHS YELLOW-GREEN N144-B. At fading: Near RHS YELLOW-GREEN 153-C.

Fragrance: Typical *Chrysanthemum*, somewhat musty.

Phyllaries:
- *Number*.—Approximately 24-27.
- *Length*.—Approximately 1 cm.
- *Width*.—Approximately 0.2 cm.
- *Texture*.—Smooth.
- *Apex shape*.—Acute.
- *Margin*.—Entire.
- *Color*.—Near RHS YELLOW-GREEN 147-B.

Peduncles:

*Peduncle length*.—Approximately 15-20 cm.

*Peduncle diameter*.—Approximately 0.5 cm.

*Angle*.—Approximately 25-30° from center of whorl.

*Color*.—Near RHS GREEN 137-B.

*Peduncle texture*.—Slightly warty.

REPRODUCTIVE ORGANS

Disc florets:

*Androecium*.—Stamens: 5 fused as a tube. Anther shape: Rounded. Anther length: Approximately 0.05 cm. Anther color: Near RHS YELLOW 13-A. Pollen quantity: In some pollen.

*Gynoecium*.—Pistil number: About 200 per flower. Pistil shape: Needle shaped. Pistil length: Approx. 0.5 cm. Style length: Approx. 0.5 cm. Style color: Near RHS YELLOW 12-B. Stigma shape: Indented. Stigma color: Near RHS YELLOW 12-B. Ovary diameter: 0.7 mm. Ovary color: Near RHS YELLOW-GREEN 149-D.

Ray Florets (if any reproductive structures present): None.

OTHER CHARACTERISTICS

Disease resistance: Unknown. No susceptibility was observed under regular growing condition.

Drought tolerance and cold tolerance: Good moderate.

Fruit/seed production: If observed.

*Seeds*.—Shape: Oblong. Color: Near RHS GREYED-GREEN 197-A.

*Fruit*.—Shape: Achene. Color: Grayed-green, RHS 197-A.

What is claimed is:

1. A new and distinct cultivar of *Chrysanthemum* plant named 'DCHRYATRED' as herein illustrated and described.

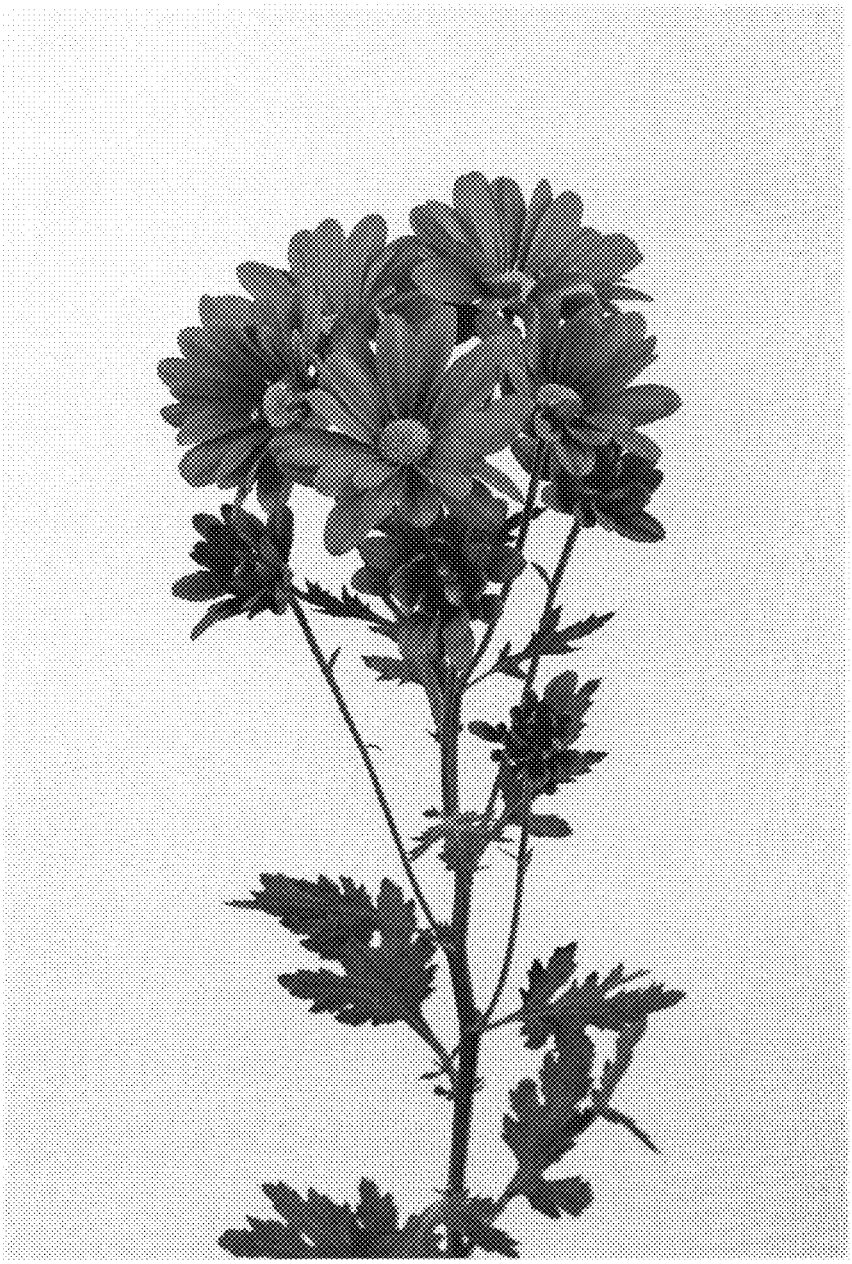

* * * * *